United States Patent [19]

Tantau

[11] Plant 4,844

[45] May 4, 1982

[54] ROSE PLANT — JP 330

[75] Inventor: Mathias Tantau, Uetersen, Fed. Rep. of Germany

[73] Assignee: Jackson & Perkins Company, Medford, Oreg.

[21] Appl. No.: 190,908

[22] Filed: Sep. 25, 1980

[51] Int. Cl.[3] ..... A01H 5/00

[52] U.S. Cl. ..... Plt./28

[58] Field of Search ..... Plt./28

*Primary Examiner*—Robert E. Bagwill

*Attorney, Agent, or Firm*—Klarquist, Sparkman, Campbell, Leigh, Whinston & Dellett

[57] ABSTRACT

A floribunda rose with blooms of red color and mild, sweet fragrance and disease resistant foliage obtained by crossing variety Dream Waltz with variety Marlena.

1 Drawing Figure

This present invention relates to a new and distinct variety of rose plant of the floribunda class which was originated by me by crossing the variety Dream Waltz with the variety Marlena, U.S. Plant Pat. No. 2,700.

The primary objective of this breeding was to produce a new rose variety combining the color of Dream Waltz with the compact growth habit of Marlena. This objective was substantially achieved along with other desirable improvements as evidenced by the following unique combination of characteristics which are outstanding in the new variety and which distinguish it from its parents as well as from all other varieties of which I am aware:

1. Large clusters of blooms.
2. A compact habit of growth, usually under 2 feet.
3. Blooms, generally of flat form, a red color near RHS 46A.
4. Disease resistant foliage.
5. A mild, sweet fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart except where ordinary dictionary significance of color is indicated.

Parentage:

*Seed parent.*—Dream Waltz.

*Pollen parent.*—Marlena, U.S. Plant Pat. No. 2,700.

Classification:

*Botanical.*—Rosa hybrid.

*Commercial.*—Floribunda.

FLOWER

Observations made from specimens grown outside at Irvine, Calif. in August.

Blooming habit: Continuous.

Bud:

*Size.*—$\frac{1}{2}''$ when petals start to unfurl.

*Form.*—Short, blunt top, globular.

*Color.*—When sepals first divide, Red 53A; when half blown, upper side of petals Red 45A; lower side of petals Red 46A.

*Sepals.*—Color: outer surface Green 138B with large overlay areas of Red-Purple 59A; surface contains numerous stipitate glands; three appendaged sepals lightly appendaged; two unappendaged sepals glandular edged.

*Receptacle.*—Color: Green 138B. Shape: funnel. Size: small. Surface: smooth.

*Peduncle.*—Length: short, Surface: glandular. Color: light green and bronzy. Strength: stiff, bending.

*Opening.*—Fold-out type, not spiral form.

Bloom:

*Size.*—Average open size $2\frac{1}{2}''$ to $3\frac{1}{2}''$.

*Borne.*—In clusters, rounded.

*Stems.*—Short.

*Form.*—When first open, flat. Permanence: retains its form to the end.

*Petalage.*—Number of petals under normal conditions: 28–30.

*Color.*—Center of flower: upper side of petals Red 45A. Reverse side of petals Red 53C. Base of petals nearly white. General tonality from a distance Red 45A.

*Variegations.*—None.

*Discoloration.*—General tonality at end of first day, no change; third day, no change.

*Fragrance.*—Slight, sweet.

Petals:

*Texture.*—Thick.

*Shape.*—Deltoid.

*Form.*—Flat.

*Arrangement.*—Imbricated. Petaloids in center: few.

*Persistence.*—Drop off cleanly.

*Lastingness.*—On the plant, long. As cut flower, long.

Reproductive parts:

*Anthers.*—Medium. Color: yellow. Arrangement: regular around styles.

*Filaments.*—Color: light green.

*Pollen.*—Gold yellow.

*Styles.*—Color: white.

*Stigmas.*—Color: very light yellow.

PLANT

Form: Bush.

Growth: Very vigorous, dwarf, branching, compact. Low growth, mostly under 2 feet at Irvine, Calif.

Foliage: Number of leaflets on normal mid-stem leaves: 5.

*Size.*—Large.

*Quantity.*—Abundant.

*Color.*—New foliage: near Red-Purple 59A. Old foliage: Green 136A.

Leaflets:

*Shape.*—Oval pointed.

*Texture.*—Leathery.

*Edge.*—Serrated.

*Serration.*—Single, small.

*Petiole.*—Rachis. Color: green. Underside: prickles, stipitate glands on upper edges.

*Stipules.*—Long, bearded.

*Disease resistance.*—Resistant to mildew, blackspot under normal growing conditions at Irvine, Calif.

Wood:

*New wood.*—Color: light green. Bark: smooth.

*Old wood.*—Color: green. Bark: smooth.

Prickles:

*Quantity.*—On main stalks from base: ordinary. On laterals from stalk: ordinary.

*Form.*—Broad base, long, hooked downward.

*Color when young.*—Brown.

*Position.*—Irregular.

Small prickles:

*Quantity.*—On main stalks, few. On laterals, few.

*Color.*—Brown.

I claim:

1. A new and distinct variety of rose plant of the floribunda class, substantially as herein shown and described, characterized particularly as to novelty by the unique combination of its compact plant, bearing red flowers in clusters and having relatively disease resistant foliage.

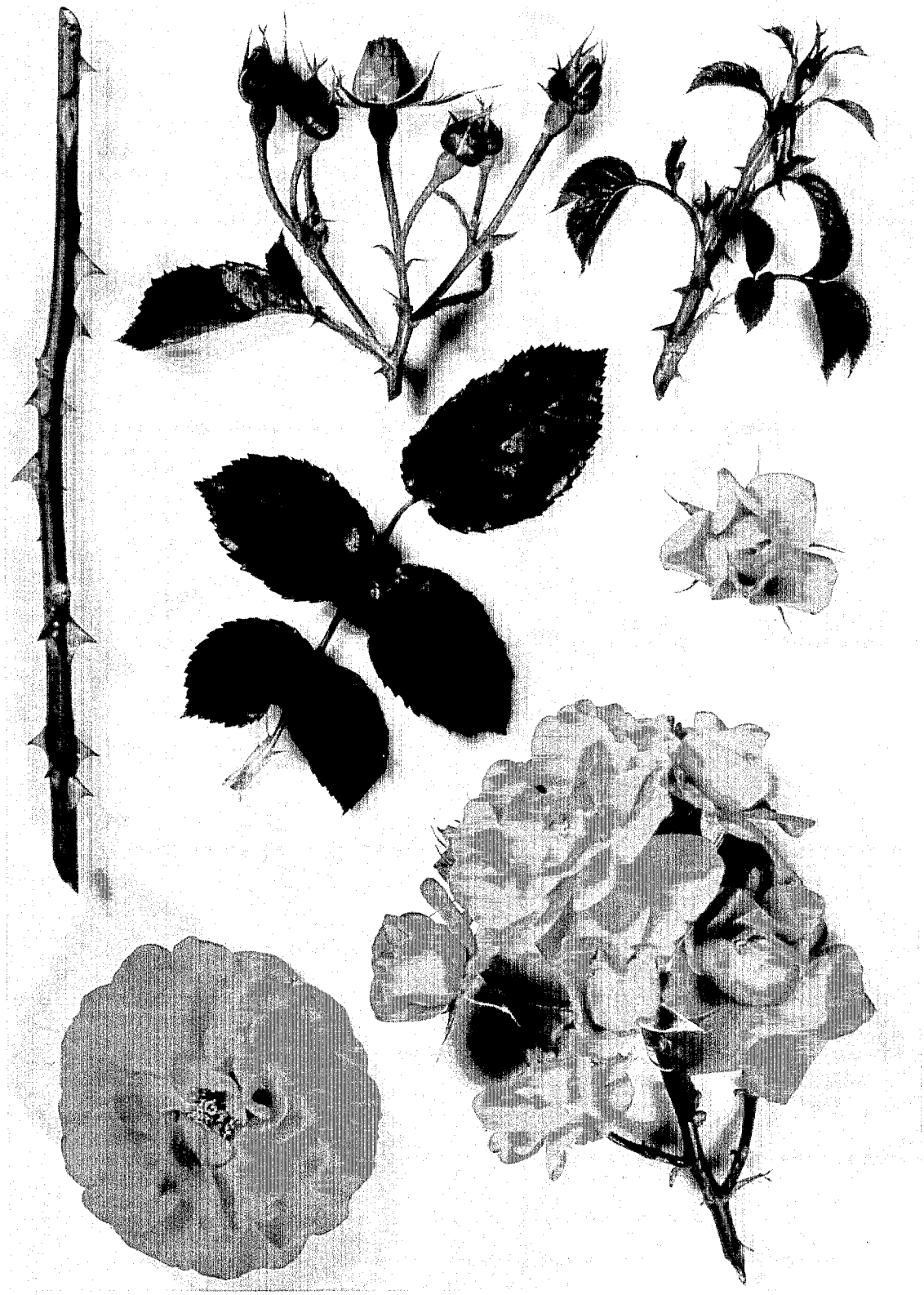

* * * * *